(12) United States Patent
Oka et al.

(10) Patent No.: US 7,750,115 B2
(45) Date of Patent: Jul. 6, 2010

(54) EPITHELIAL CELL GROWTH PROMOTER

(75) Inventors: Syuichi Oka, Tsukuba (JP); Akinori Tsuruda, Tsukuba (JP); Yasuhiro Kawano, Tsukuba (JP); Mitsuo Suzuki, Tokyo (JP); Satoshi Nakazato, Tokyo (JP)

(73) Assignee: Patent Technology Development, Inc., Tokyo (JP)

( * ) Notice: Subject to any disclaimer, the term of this patent is extended or adjusted under 35 U.S.C. 154(b) by 562 days.

(21) Appl. No.: 10/594,736

(22) PCT Filed: Mar. 28, 2005

(86) PCT No.: PCT/JP2005/005677

§ 371 (c)(1),
(2), (4) Date: Nov. 7, 2006

(87) PCT Pub. No.: WO2005/095441

PCT Pub. Date: Oct. 13, 2005

(65) Prior Publication Data

US 2007/0213276 A1    Sep. 13, 2007

(30) Foreign Application Priority Data

Mar. 31, 2004  (JP) ............... 2004-108449
Jul. 7, 2004   (JP) ............... 2004-200862

(51) Int. Cl.
*C07K 7/06* (2006.01)
(52) U.S. Cl. .................. 530/330; 514/17
(58) Field of Classification Search .......... 530/330, 530/331; 514/17
See application file for complete search history.

(56) References Cited

U.S. PATENT DOCUMENTS

| 4,139,619 | A |   | 2/1979 | Chidsey, III |
| 5,039,662 | A | * | 8/1991 | Schasteen ............... 514/17 |
| 5,092,885 | A | * | 3/1992 | Yamada et al. .......... 623/23.76 |
| 6,015,689 | A | * | 1/2000 | Okado et al. ........... 435/69.1 |
| 6,074,832 | A | * | 6/2000 | Venta et al. ............ 435/6 |
| 6,093,797 | A |   | 7/2000 | Abajian et al. |
| 6,344,541 | B1| * | 2/2002 | Bass et al. ............. 530/324 |
| 2002/0168354 | A1 |   | 11/2002 | Mochly-Rosen |
| 2003/0157132 | A1 |   | 8/2003 | Itami et al. |
| 2003/0176354 | A1 |   | 9/2003 | Abajian et al. |
| 2007/0026021 | A1 | * | 2/2007 | Fraser et al. ........... 424/250.1 |
| 2007/0203060 | A1 | * | 8/2007 | Sidelman ............... 514/12 |

FOREIGN PATENT DOCUMENTS

| EP | 0 640 333 | 3/1995 |
| EP | 1 132 396 | 9/2001 |
| GB | 2 321 852 | 8/1998 |
| WO | 00/64486  | 11/2000 |
| WO | 01/68145  | 9/2001 |
| WO | 01/75454  | 10/2001 |
| WO | 02/102832 | 12/2002 |
| WO | 03/093314 | 11/2003 |

OTHER PUBLICATIONS

Abstract of Minoru (JP 07-101834, issued Apr. 1995).*
Abstract of Yoshikawa (WO 00/29425; issued May 2000).*
Abstract of Kenji (JP 10-279501, issued Oct. 1998).*
Tsuruda et al., "A Short Peptide GPIGS Promotes Proliferation of Hair Bulb Keratinocytes and Accelerates Hair Regrowth in Mice", *Biol. Pharm. Bull.*, vol. 28, No. 3, pp. 485-489, 2005.
Nikkei Business Daily, p. 18, Mar. 2, 2004.
Abstract of Imamura (JP 2002-326913, published Nov. 15, 2002).
Abstract of Mizushima (JP 11-246359, published Sep. 14, 1999).
Abstract of Ikeda (WO 02/19975, published Mar. 14, 2002).
Abstract of Suzuki (JP 2000-309521, published Nov. 7, 2000).
Abstract of Sakai (JP 2003-137807, published May 14, 2003).
Abstract of Burchardt (WO 03/007980, published Jan. 30, 2003).
Pages 1, 725, and 726 of Galeotti (WO 01/31019, published May 3, 2001).
Abstract of Itami (WO 01/58459, published Aug. 16, 2001).

* cited by examiner

*Primary Examiner*—David Lukton
(74) *Attorney, Agent, or Firm*—Wenderoth, Lind & Ponack, L.L.P.

(57) ABSTRACT

It is intended to provide a novel oligopeptide which can be relatively easily produced, has not only a hair growth-stimulating effect but also an effect of promoting the growth of epithelial cells (for example, skin regeneration) and can easily pass through the horny layer to thereby reach the desired target cells in which its effects are to be exerted. Namely, water-soluble oligopeptides containing a proryl isoleucyl glycyl unit or an isoleucyl glycyl serine unit and having from 3 to 7 amino acids and water-soluble salts thereof.

4 Claims, 11 Drawing Sheets

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial
<220> FEATURE:
<223> OTHER INFORMATION: A synthesized oligopeptide
<220> FEATURE:
<221> NAME/KEY: PEPTIDE
<222> LOCATION: (1)..(4)
<223> OTHER INFORMATION: A partial structure of GPIGS peptide

<400> SEQUENCE: 1

Gly Pro Ile Gly
1

<210> SEQ ID NO 2
<211> LENGTH: 4
<212> TYPE: PRT
<213> ORGANISM: Artificial
<220> FEATURE:
<223> OTHER INFORMATION: A synthesized oligopeptide
<220> FEATURE:
<221> NAME/KEY: PEPTIDE
<222> LOCATION: (1)..(4)
<223> OTHER INFORMATION: A partial structure of GPIGS peptide

<400> SEQUENCE: 2

Pro Ile Gly Ser
1

<210> SEQ ID NO 3
<211> LENGTH: 5
<212> TYPE: PRT
<213> ORGANISM: Artificial
<220> FEATURE:
<223> OTHER INFORMATION: A synthesized oligopeptide
<220> FEATURE:
<221> NAME/KEY: PEPTIDE
<222> LOCATION: (1)..(5)
<223> OTHER INFORMATION:

<400> SEQUENCE: 3

Gly Pro Ile Gly Ser
```

```
1               5

<210> SEQ ID NO 4
<211> LENGTH: 5
<212> TYPE: PRT
<213> ORGANISM: Artificial
<220> FEATURE:
<223> OTHER INFORMATION: A synthesized oligopeptide
<220> FEATURE:
<221> NAME/KEY: PEPTIDE
<222> LOCATION: (1)..(4)
<223> OTHER INFORMATION: The C-terminal Ser residue in GPIGS is replaced
      with Thr.

<400> SEQUENCE: 4

Gly Pro Ile Gly Thr
1               5

<210> SEQ ID NO 5
<211> LENGTH: 6
<212> TYPE: PRT
<213> ORGANISM: Artificial
<220> FEATURE:
<223> OTHER INFORMATION: A synthesized oligopeptide
<220> FEATURE:
<221> NAME/KEY: PEPTIDE
<222> LOCATION: (2)..(6)
<223> OTHER INFORMATION: A derivertive of a GPIGS peptide in which the
      N-terminal Gly residue is modified with Ala.

<400> SEQUENCE: 5

Ala Gly Pro Ile Gly Ser
1               5

<210> SEQ ID NO 6
<211> LENGTH: 6
<212> TYPE: PRT
<213> ORGANISM: Artificial
<220> FEATURE:
<223> OTHER INFORMATION: A synthesized oligopeptide
<220> FEATURE:
<221> NAME/KEY: PEPTIDE
<222> LOCATION: (2)..(6)
<223> OTHER INFORMATION: A derivertive of a GPIGS peptide in which the
      N-terminal Gly residue is modified with Ser.

<400> SEQUENCE: 6

Ser Gly Pro Ile Gly Ser
1               5

<210> SEQ ID NO 7
<211> LENGTH: 7
<212> TYPE: PRT
<213> ORGANISM: Artificial
<220> FEATURE:
<223> OTHER INFORMATION: A synthesized oligopeptide
<220> FEATURE:
<221> NAME/KEY: PEPTIDE
<222> LOCATION: (3)..(7)
<223> OTHER INFORMATION: A derivertive of a GPIGS peptide in which the
      N-terminal Gly residue is modified with GlySer.

<400> SEQUENCE: 7

Gly Ser Gly Pro Ile Gly Ser
1               5
```

EPITHELIAL CELL GROWTH PROMOTER

This application is a 371 of PCT/JP05/05677, filed Mar. 28, 2005, which claims foreign priority to JP 2004-108449, filed Mar. 31, 2004 and JP 2004-200862, filed Jul. 7, 2004.

TECHNICAL FIELD

The present invention relates to a novel water-soluble oligopeptide having epithelial cell growth-promoting effect such as hair growth-promoting effect, skin regeneration-promoting effect, therapeutic effect on skin ulcer, and therapeutic effect on mucosal injury. More particularly, the present invention relates to a water-soluble oligopeptide and a water-soluble salt thereof comprising 3 to 7 amino acid units containing a particular amino acid sequence and to an epithelial cell growth promoter comprising them as an active ingredient.

BACKGROUND TECHNOLOGY

Recently, the control mechanisms of hair growth and hair loss have been elucidated, while a variety of new hair growth agents such as novel compounds having the hair growth-promoting effect, ingredients based on genetic research, combinations of the Chinese traditional medicine system and others have been proposed along with increased public concern for hair growth agents.

FIG. 1 is an illustrative diagram showing a hair cycle that repeats hair growth and hair loss. A normal hair has a hair papilla 3 in a hair root 2 of a hair body 1 thereof and has a trichogen cell 4 above the hair papilla 3. The hair body 1 grows up, enters a regression phase (catagen) and stops growing in approximately 2 to 3 weeks. Then, it enters a resting phase (telogen) for 2 to 3 months. In the meantime, the hair root 2 continues its activities and generates a new hair body 1'. This new hair body 1' proceeds to enter a growth phase (anagen) and loses the old hair body 1. It further keeps growing and regenerates an original hair form in approximately 5 to 6 years.

Hair growth agents have the effect of promoting trichogen cell growth in each phase of such a hair cycle, inducing the anagen phase in the telogen phase, prolonging the anagen phase, or delaying shift to the catagen phase and perform the promotion of hair growth or the inhibition of hair loss.

For example, a hair growth agent comprising 6-(1-piperidinyl)-2,4-pyrimidinediamine-3-oxide (minoxidil) as an active ingredient (see U.S. Pat. No. 4,139,619), a hair growth composition comprising 1 to 6% by mass of minoxidil, polyhydric alcohol, ethanol, pyridoxin hydrochloride, and water (see Japanese Patent Laid-Open No. 2002-326913), a hair growth agent comprising a fibroblast growth factor-10 (FGF-10) as an active ingredient (see Japanese Patent Laid-Open No. 10-279501), a pilatory comprising particular fatty acid ester, ether, monoglyceride sulfate, or monoalkyl glyceryl ether sulfate as an active ingredient (see Japanese Patent Laid-Open No. 11-246359), a hair growth agent comprising a CRF1 receptor antagonist as an active ingredient (see the pamphlet of International Publication No. WO 02/019975), an aerosol preparation for hair growth containing: a gelled composition for aerosol comprising a crude drug extract with blood circulation-promoting effect and vitamin or a derivative thereof as active ingredients and having a water-soluble polymer mixed therewith; and a propellant (see Japanese Patent Laid-Open No. 7-101834) and elsewhere have previously been proposed as such hair growth agents.

Alternatively, an oral hair growth agent comprising, as an active ingredient, a peptide represented by the formula, $R^1$-Met-Ile-X$R^2$ (in the formula, X represents Trp, Phe, Trp-Leu, Phe-Leu, Tyr-Leu, Ile-Leu, or Leu-Leu; $R^1$ represents a hydrogen atom or an amino-protecting group; and $R^2$ represents a hydroxyl- or carboxyl-protecting group) or a pharmacologically acceptable salt is known as a special hair growth agent (see the pamphlet of International Publication No. WO 00/29425).

In addition, information from very recent newspaper has reported the release of a hair growth agent having 6-benzyl aminopurine (cytopurine) in combination with pentadecane (see the article issued on Mar. 2, 2004, Nikkei Business Daily).

These hair growth agents have their own advantages, and some of them are approved to exhibit significantly effects. However, they cannot completely respond to all symptoms and certain raw materials thereof are difficult to obtain so that they are not necessarily adequate for practical applications. Therefore, the appearance of a novel hair growth agent exhibiting excellent effects has been demanded in this field.

On the other hand, a skin lotion for anti-aging consisting of a polymerization product with an average molecular weight of 280 to 20000 of a tripeptide composed of one glycine residue and two other amino acid residues in a degradation product of collagen or gelatin obtained by collagenase (see Japanese Patent Laid-Open No. 2000-309521), a collagen-producing promoter comprising a mixture of tripeptides consisting of (Gly-Ala-Arg), (Gly-Ala-Hyp), (Gly-Ala-Lys), (Gly-Pro-Ala), (Gly-Pro-Arg), (Gly-Pro-Hyp), and (Gly-Pro-Ser) as an active ingredient (see Japanese Patent Laid-Open No. 2003-137807) and elsewhere are known as physiologically active substances comprising an oligopeptide or a polymerization product thereof as an active ingredient. However, no epithelial cell growth promoter comprising a tripeptide as an active ingredient has been proposed so far.

DISCLOSURE OF THE INVENTION

An object of the present invention is to provide a novel water-soluble oligopeptide that can be produced in a relatively simple way, has not only the hair growth-promoting effect but also the epithelial cell growth-promoting effect such as skin regeneration, and can easily pass through the stratum corneum to reach and act on a desired target cell.

The inventors have conducted intensive studies to develop chemicals useful as a hair growth agent and, as a result, have arrived at a discovery that an active substance exhibiting excellent hair growth effect is present in an extract from the culture supernatant of bacteria of the genus *Bacillus*, that the hair growth effect results from a particular oligopeptide structure in this active substance, and that any particular polypeptide having this oligopeptide structure not only exhibits desired hair growth effect but also exhibits the effect of promoting cell regeneration in skin transplantation or in the restoration of skin ulcer or aging skin. The inventors have further arrived at a discovery that a water-soluble oligopeptide having particular amino acid units exhibits excellent epithelial cell growth-promoting effect leading to completion of the present invention on the basis of these discoveries.

Namely, the present invention provides a water-soluble oligopeptide and a water-soluble salt thereof having 3-7 amino acid units containing a prolyl-isoleucyl-glycyl unit or an isoleucyl-glycyl-serine unit, and an epithelial cell growth promoter comprising at least one selected from the water-soluble oligopeptide and the water-soluble salt thereof as an active ingredient.

The effect of the water-soluble oligopeptide in the epithelial cell growth promoter of the present invention is exerted not only in the oligopeptide per se but also in a polypeptide having these oligopeptide units as its molecular structure unit. However, those having a molecular weight of 500 or more are rendered slightly soluble in water so that they are not preferable as a hair growth agent.

Among such water-soluble oligopeptides, a tripeptide includes isoleucyl-glycyl-serine and prolyl-isoleucyl-glycine. And, a tetrapeptide is exemplified, for example, by this tripeptide with an amino acid residue such as a glycyl, alanyl, arginyl, asparagyl, lysyl, seryl, valyl, or glutamyl group bonded to the front or rear, of which glycyl-prolyl-isoleucyl-glycine (SEQ ID NO: 1) and prolyl-isoleucyl-glycyl-serine (SEQ ID NO: 2) are preferred.

A pentapeptide is exemplified, for example, by the glycyl-prolyl-isoleucyl-glycyl (SEQ ID NO: 1) group with an amino acid residue such as a seryl group or a threonyl group bonded to the front or rear, of which glycyl-prolyl-isoleucyl-glycyl-serine (SEQ ID NO: 3) and glycyl-prolyl-isoleucyl-glycyl-threonine (SEQ ID NO: 4) are preferred.

Further, preferable hexapeptide and heptapeptide are any of those having the above-mentioned pentapeptide unit at the carboxyl terminus, such as, for example, alanyl-glycyl-prolyl-isoleucyl-glycyl-serine (SEQ ID NO: 5), seryl-glycyl-prolyl-isoleucyl-glycyl-serine (SEQ ID NO: 6), glycyl-seryl-glycyl-prolyl-isoleucyl-glycyl-serine (SEQ ID NO: 7) and the like.

The water-soluble oligopeptide of the present invention may be in a free form or a water-soluble salt form. This water-soluble salt includes, for example, sodium salt, potassium salt, lithium salt, ammonium salt and the like.

The oligopeptide of the present invention can be produced by reacting a raw material amino acid having the α-amino group protected and an amino acid having the carboxyl group protected by any conventional method for forming a peptide bond in synthesis of a polypeptide such as, for example, a condensation method, active ester method, azide method, mixed acid anhydride method and others, so as to form a peptide, which is in turn repeatedly subjected to the step of eliminating the protecting groups.

This condensation method is the most general method for forming a peptide bond. In this method, for example, dicyclohexylcarbodiimide (DCC), diisopropylcarbodiimide (DIPC), N-ethyl-N'-3-dimethylaminopropylcarbodiimide (WSCl) and hydrochlorides thereof (WSCl.HCl), benzotriazole-1-yl-tris(dimethylamino)phosphonium hexafluorophosphide (BOP), diphenylphosphoryl diazide (DPPA) and the like are used alone as a condensing agent or in combination with N-hydroxysuccinimide (HONSu), 1-hydroxybenzotriazole (HOBt), or 3-hydroxy-4-oxo-3,4-dihydro-1,2,3-benzotriazine (HOObt).

In the active ester method, for example, p-nitrophenyl ester (ONp), N-hydroxysuccinimide ester (ONSu), pentafluorophenyl ester (OPfp) and the like can be used as an active ester.

The azide method is a method in which an amino acid or a peptide is reacted with anhydrous hydrazine to form a corresponding hydrazide, and is known as a segment condensation method with low racemization.

Furthermore, the mixed acid anhydride method is a method in which isobutyloxycarbonyl chloride, diethylacetyl chloride, trimethylacetyl chloride and the like can be used to form a mixed anhydride of the carboxyl group of an amino acid, and is advantageous since it can strongly activate the carboxyl group at low temperatures.

On the other hand, those easily eliminated by acid treatment, hydrolysis, or catalytic reduction are used as protecting groups for an amino acid. Among such protecting groups, a protecting group for an α-amino group includes benzyloxycarbonyl group, tert-butoxycarbonyl group, 9-fluorenylmethoxycarbonyl group, 3-nitro-2-pyridinesulfenyl group, methoxybenzyloxycarbonyl group and the like. The protection of a carboxyl group is performed with methyl or ethyl ester, benzyl ester, tert-butyl ester, phenacyl ester, or the like.

In the case of an α-amino acid having a hydroxyl group at the side chain, this hydroxyl group has to be protected. The protecting group is suitably a benzyl group that is easily eliminated by catalytic reduction with a platinum black catalyst or by strong acid treatment and, a tert-butyl group that is easily eliminated by weak acid treatment.

Such an α-amino acid ester or a raw material amino acid with the amino group or hydroxyl group protected can be easily obtained as a commercial product.

The production of the oligopeptide of the present invention can be performed by both of a liquid phase method wherein a raw material amino acid or a derivative thereof is evenly dissolved in a solvent to effect the reaction, and a solid phase method wherein a peptide chain is elongated on an insoluble resin, and is advantageously performed with an automatic solid-phase synthesizer. According to this method, a desired oligopeptide can be obtained in a short time and in a high purity.

The novel oligopeptide or water-soluble salt thereof of the present invention is obtained as a racemic body and can also be obtained, according to desire, as a substance having optical activity by subjecting the racemic body to optical resolution by any conventional method. This optical resolution can be performed by a method in which a diastereomer formed between the racemic amino acid and an appropriate optically active substance is subjected to fractional crystallization, a method using an enzyme, or a method performed by high-performance liquid chromatography (HPLC) using a chiral carrier.

The oligopeptide of the present invention is soluble in water or alcohol compounds. This can be identified by mass spectrometry, an infrared absorption spectrum, or high-performance liquid chromatography.

The oligopeptide of the present invention has the effect of directly promoting hair bulb keratinocytes (HBK) growth or, particularly, trichogen cell growth, that is, hair growth-promoting effect. In addition, it has the effect of directly promoting epidermal cell growth and is thus useful in the graft of cultured skin or in the treatment of skin ulcer and skin defective injury. Therefore, the oligopeptide of the present invention can be used as an epithelial cell growth promoter.

A preparation of the epithelial cell growth promoter of the present invention is obtained by dissolving the above-mentioned oligopeptide serving as an active ingredient in a concentration of 0.0001 to 5% by mass in an aqueous medium. A mixture solvent of water and a water-soluble organic solvent are preferable as the aqueous medium used in this procedure.

For example, alcohol compounds such as ethyl alcohol, polyhydric alcohol compounds such as ethylene glycol, diethylene glycol, dipropylene glycol, glycerin, and 1,3-butylene glycol, polar organic solvents such as dimethylformamide and dimethylsulfoxide are used as the water-soluble organic solvent. These can be used alone or can be used as a combination of two kinds or more. A preferable aqueous solvent is a mixture solvent of water, propylene glycol, and ethyl alcohol.

It is optional according to desire that this epithelial cell growth promoter of the present invention contains other compounds having the hair growth-promoting effect such as, for example, minoxidil, carpronium chloride, glyceryl pentadecanoate, tocopherol acetate, piroctone olamine, glycyrrhizic acid, isopropylmethylphenol, hinokitiol, *Swertia japonica* extracts, *Capsicum* tincture, vitamins including, for example, vitamin A, vitamin B, vitamin C, vitamin D, vitamin E, vitamin F, vitamin H, vitamin K, vitamin P, and vitamin U, pantothenyl alcohol, carnitine, ferulic acid, γ-oryzanol, lipoic acid, orotic acid, or derivatives thereof. These compounds are mixed in an amount ranging from 0.005 to 10% by mass or, preferably, 0.01 to 2.0% by mass, into the epithelial cell growth promoter of the present invention.

It is optional according to desire that the epithelial cell growth promoter of the present invention is further admixed with additives conventionally used in usual lotions such as flavors, coloring agents, pH regulators, disinfectants, surfactants, propellants and the like. The amount of these additives ranges from 0.001 to 5% by mass or, preferably, 0.01 to 2.0% by mass.

The epithelial cell growth promoter of the present invention is used by repeatedly applying approximately once to five times a day to the head skin or to the affected skin.

Considering that the epithelial cell growth promoter of the present invention can be effective to dose-dependently promote HBK growth, the oligopeptide contained therein as an active ingredient could be confirmed to have epithelial cell growth-promoting effect.

Moreover, the oligopeptide of the present invention exhibits selective growth-promoting effect on epithelial cells and is therefore advantageous without the possibility of growth of other cells such as, for example, cancer cells.

BEST MODE FOR CARRYING OUT THE INVENTION

In the following, the best mode for carrying out the present invention will be described by way of Examples. However, the present invention is not intended to be limited by them in any way.

EXAMPLE 1

Tetrahydrofuran and dicyclohexylcarbodiimide were used as a solvent and a condensing agent, respectively, to produce benzyl ester of N-Fmoc-isoleucyl-glycyl-serine by successively reacting benzyl ester of serine having the hydroxyl group protected with a tert-butyl group, glycine having the α-amino group protected with a 9-fluorenylmethoxycarbonyl group (hereinafter, abbreviated to Fmoc group), and isoleucine having the α-amino group protected with an Fmoc group in the presence of triethylamine by use of an automatic solid-phase synthesizer (Model "Syro 2000", manufactured by MultiSynTech Co.).

After the termination of reaction, the elimination of the protecting groups and the hydrolysis of the ester were performed by treating the generated intermediate with hydrofluoric acid in a mixture solvent of methyl alcohol and dioxane (3:1 by volume) and purifying it by chromatography, to obtain racemic isoleucyl-glycyl-serine. In this case, the yield thereof was approximately 46%.

Next, this tripeptide was passed through a $C_{18}$ column [Model "HP1100" (3.0×250 mm), manufactured by Hewlett-Packard Co.] (the column was used for purity analysis in Examples 2 to 4 below), and components adsorbed thereon were eluted at a flow rate of 0.4 ml/minute for 20 minutes with a solution of acetonitrile in a concentration ranging from 0 to 30% containing 0.1% trifluoroacetic acid. As a result, the tripeptide was eluted with a retention time of 11.671 minutes in a purity of 95.87%.

Figure 1:
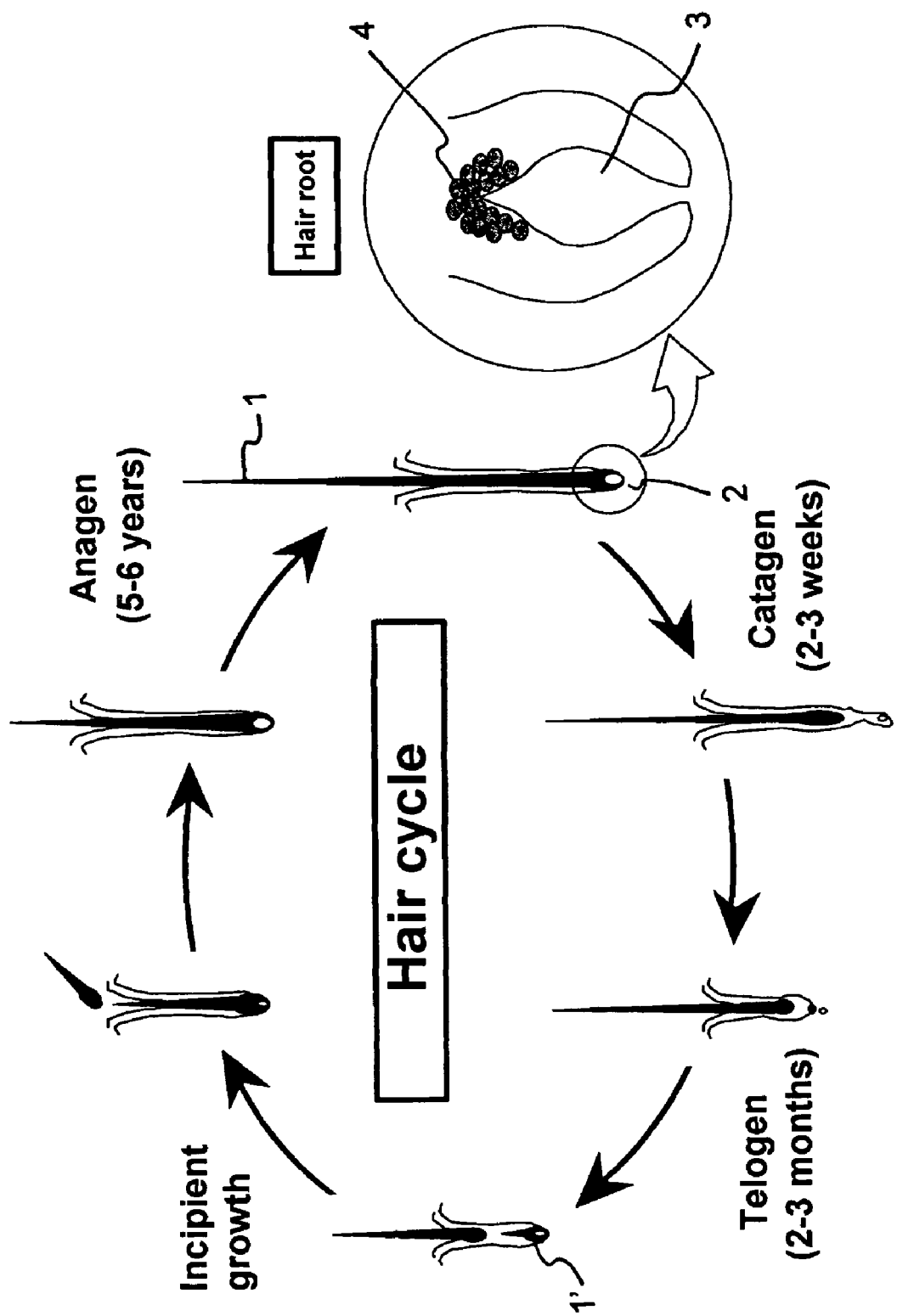
FIG. 1 is an illustrative diagram showing a hair cycle of hair growth and hair loss.
Figure 2:
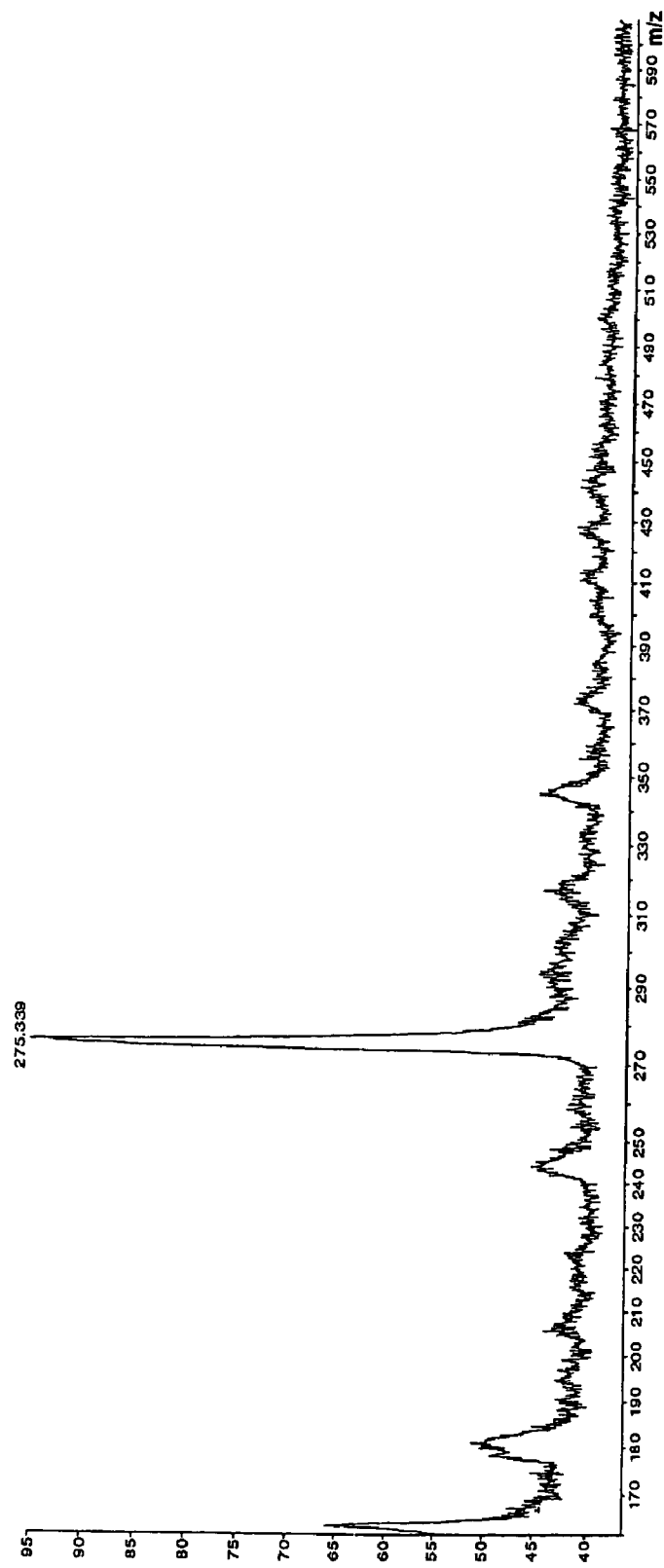
FIG. 2 is a mass spectrum of the tripeptide obtained in Example 1.

The mass of this tripeptide was analyzed with a MALDI-MS mass spectrometer [Model "Dynamo", manufactured by Thermo BioAnalysis Corp.] (the mass spectrometer was used for mass spectrometry in Examples 2 to 4 below) to show that the mass (m/z, $MH^+$) was m/z 275.339. The result of this mass spectrometry is shown in FIG. 2.

EXAMPLE 2

Benzyl ester of glycine, isoleucine having the α-amino group protected with an Fmoc group, and proline having the α-amino group protected with an Fmoc group were used to produce racemic prolyl-isoleucyl-glycine by totally the same procedure as in Example 1. In this case, the yield thereof was approximately 40%.

Next, this tripeptide was passed through a $C_{18}$ column, and components adsorbed thereon were eluted at a flow rate of 0.4 ml/minute for 20 minutes with a solution of acetonitrile in a concentration ranging from 0 to 30% containing 0.1% trifluoroacetic acid. As a result, the tripeptide was eluted with a retention time of 14.052 minutes in a purity of 95.93%.

Figure 3:
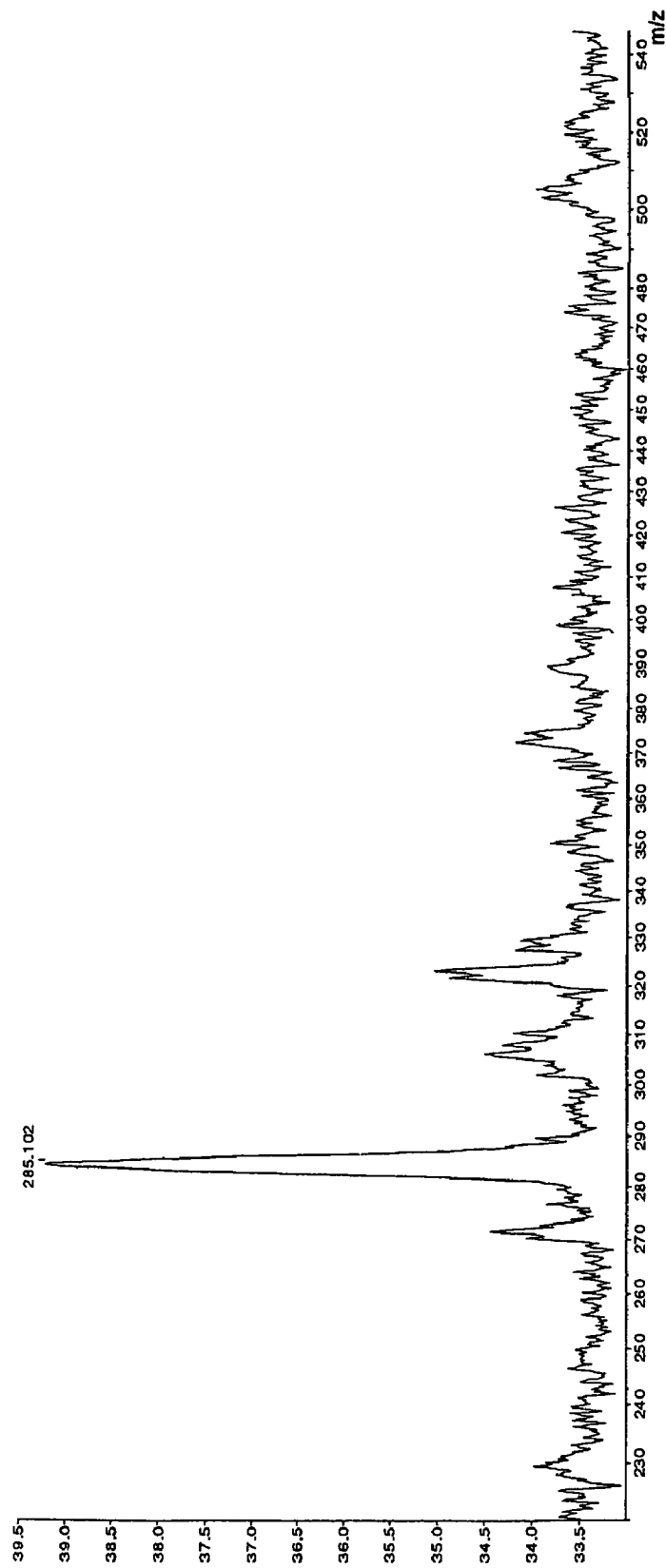
FIG. 3 is a mass spectrum of the tripeptide obtained in Example 2.

The mass of this tripeptide was analyzed to show that the mass (m/z, $MH^+$) was m/z 285.102. The result of this mass spectrometry is shown in FIG. 3.

EXAMPLE 3

Benzyl ester of serine having the hydroxyl group protected with a tert-butyl group, glycine having the α-amino group protected with an Fmoc group, isoleucine having the α-amino group protected with an Fmoc group, and proline having the α-amino group protected with an Fmoc group were used to produce racemic prolyl-isoleucyl-glycyl-serine (SEQ ID NO: 2) by totally the same procedure as in Example 1. In this case, the yield thereof was approximately 54%.

Next, this tetrapeptide was passed through a $C_{18}$ column, and components adsorbed thereon were eluted at a flow rate of 0.4 ml/minute for 20 minutes with a solution of acetonitrile in a concentration ranging from 0 to 40% containing 0.1% trifluoroacetic acid. As a result, the tetrapeptide was eluted with a retention time of 12.313 minutes in a purity of 95.11%.

Figure 4:
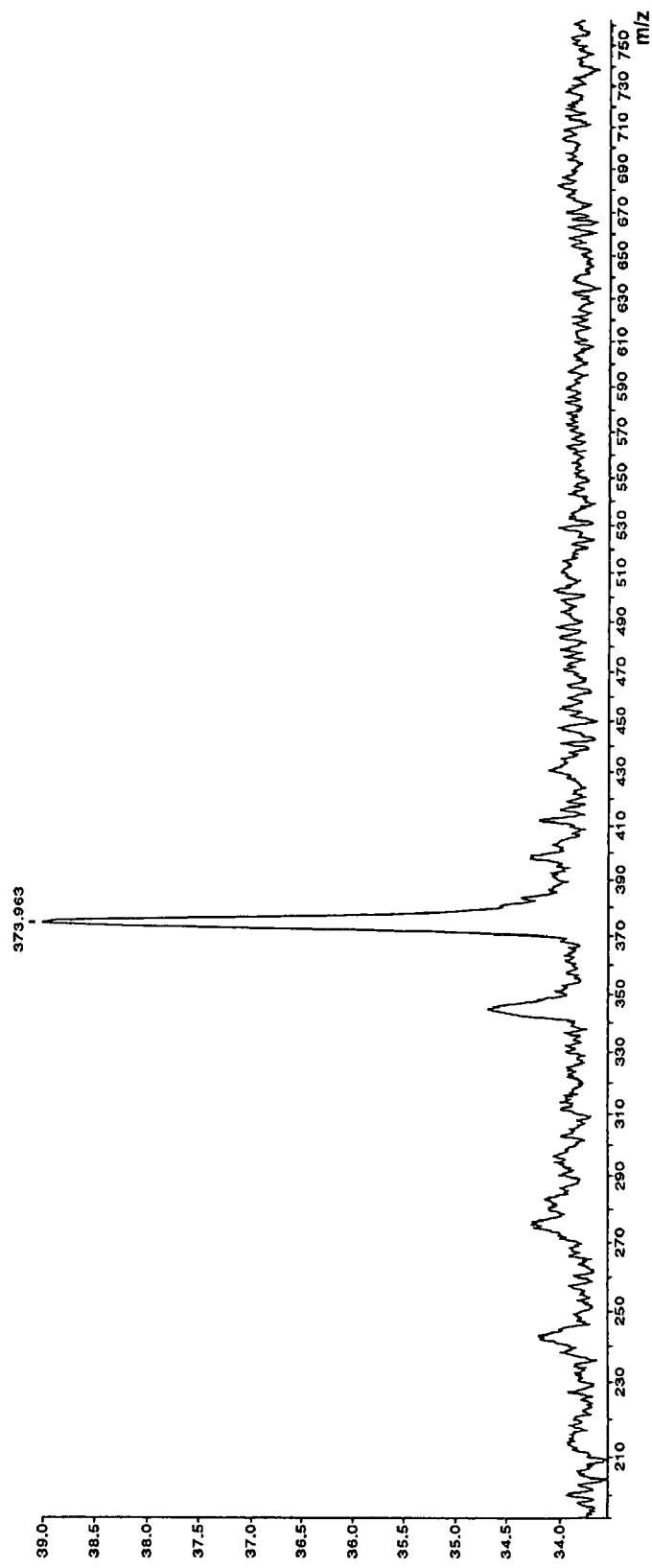
FIG. 4 is a mass spectrum of the tetrapeptide obtained in Example 3.

The mass of this tetrapeptide was analyzed to show that the mass (m/z, MH$^+$) was m/z 373.963. The result of this mass spectrometry is shown in FIG. 4.

EXAMPLE 4

Benzyl ester of glycine, isoleucine having the α-amino group protected with an Fmoc group, proline having the α-amino group protected with an Fmoc group, and glycine having the α-amino group protected with an Fmoc group were used to produce racemic glycyl-prolyl-isoleucyl-glycine (SEQ ID NO: 1) by totally the same procedure as in Example 1. In this case, the yield thereof was approximately 48%.

Next, this tetrapeptide was passed through a $C_{18}$ column, and components adsorbed thereon were eluted at a flow rate of 0.4 ml/minute for 20 minutes with a solution of acetonitrile in a concentration ranging from 5 to 40% containing 0.1% trifluoroacetic acid. As a result, the tetrapeptide was eluted with a retention time of 11.648 minutes in a purity of 99.60%.

Figure 5:
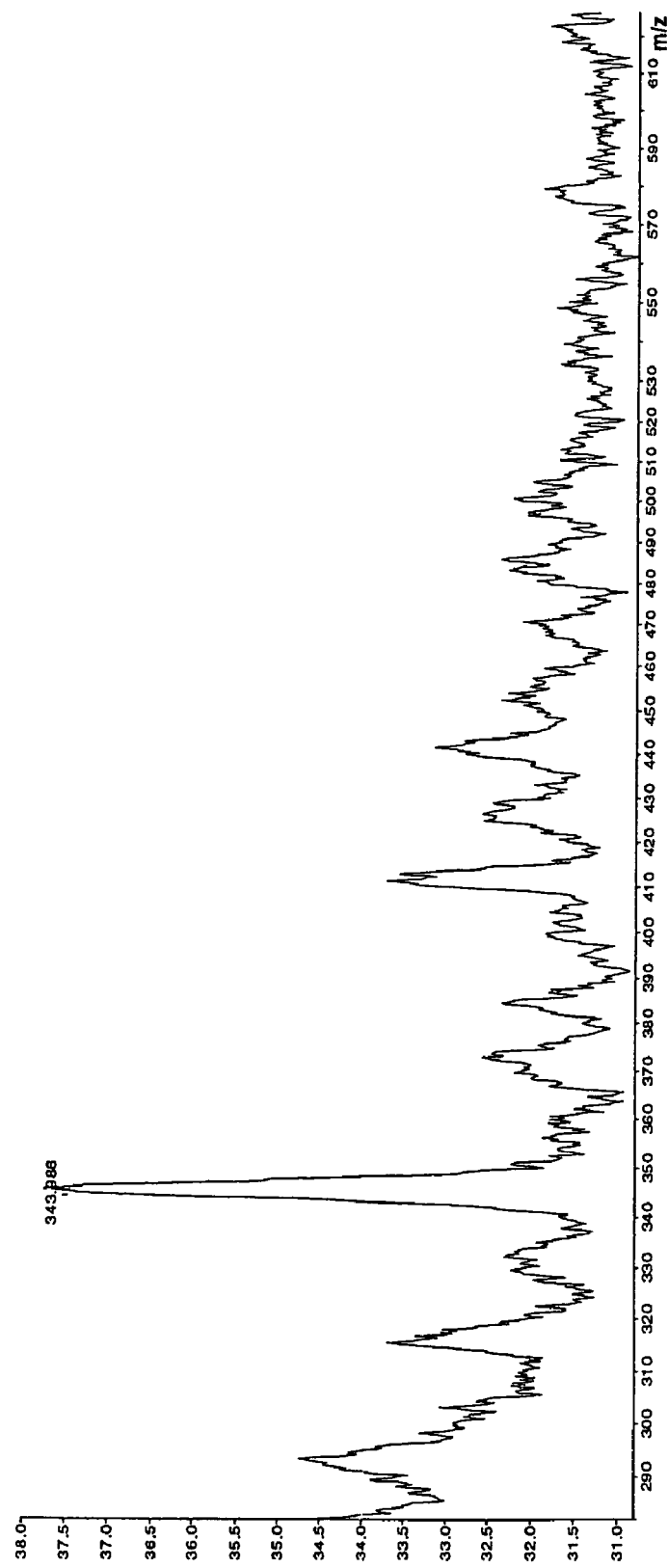
FIG. 5 is a mass spectrum of the tetrapeptide obtained in Example 4.

The mass of this tetrapeptide was analyzed to show that the mass (m/z, MH$^+$) was m/z 343.986. The result of this mass spectrometry is shown in FIG. 5.

EXAMPLE 5

Tetrahydrofuran and dicyclohexylcarbodiimide were used as a solvent and a condensing agent, respectively, to produce benzyl ester of N-Fmoc-glycyl-prolyl-isoleucyl-glycyl-serine (SEQ ID NO: 3) by successively reacting benzyl ester of serine having the hydroxyl group protected with a tert-butyl group, glycine having the α-amino group protected with an Fmoc group, isoleucine having the α-amino group protected with an Fmoc group, proline having the α-amino group protected with an Fmoc group, and glycine having the α-amino group protected with an Fmoc group in the presence of triethylamine by use of an automatic solid-phase synthesizer (Model "Syro 2000", manufactured by MultiSynTech Co.).

After the termination of reaction, the elimination of the protecting groups and the hydrolysis of the ester were performed by treating the generated intermediate with hydrofluoric acid in a mixture solvent of methyl alcohol and dioxane (3:1 by volume) and purifying it by chromatography, to give racemic glycyl-prolyl-isoleucyl-glycyl-serine. In this case, the yield thereof was approximately 40%.

Next, this pentapeptide was passed through a $C_{18}$ column [Model "Discovery $C_{18}$" (4.6×250 mm), manufactured by Supelco], and components adsorbed thereon were eluted at a flow rate of 1.5 ml/minute for 20 minutes with a solution of acetonitrile in a concentration ranging from 2 to 22% containing 0.1% trifluoroacetic acid. As a result, the pentapeptide was eluted with a retention time of 9.761 minutes in a purity of 96.9%.

Figure 6:
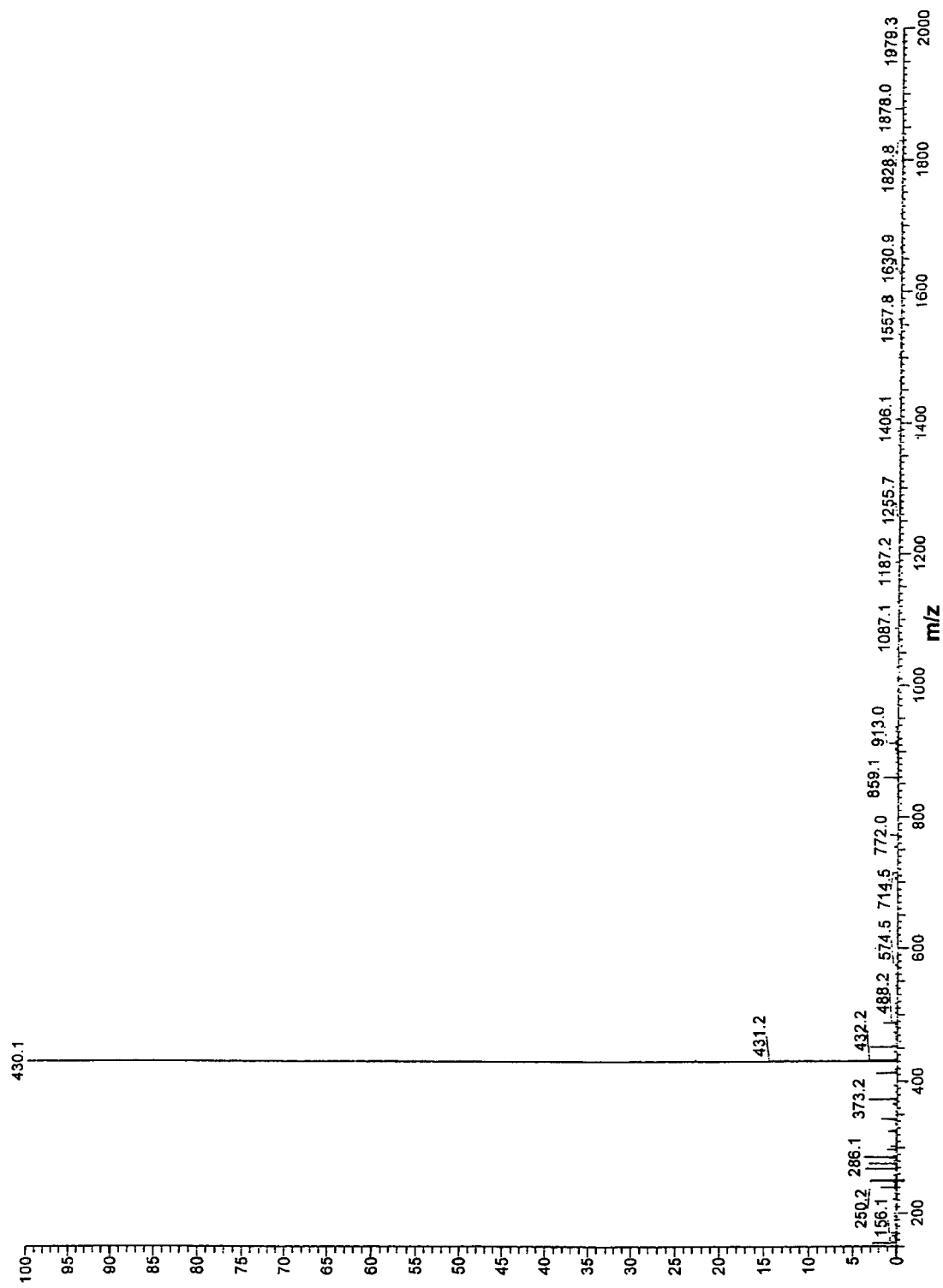
FIG. 6 is a mass spectrum of the pentapeptide obtained in Example 5.

The mass of this pentapeptide was analyzed with an LC-MS mass spectrometer [LC portion: Model "Agilent 1100 Series", manufactured by Agilent Technologies, Ltd.; MS portion: Model "Thermofinnigan LCQ advantage (software Xcalibur)", manufactured by Thermo Electron Corp.] by cation measurement using an electrospray ionization method to show that the mass (m/z, MH$^+$) was m/z 430.1. The result of this mass spectrometry is shown in FIG. 6.

EXAMPLE 6

Racemic glycyl-prolyl-isoleucyl-glycyl-threonine (SEQ ID NO: 4) was produced by totally the same procedure as in Example 1 except that benzyl ester of threonine having the hydroxyl group protected with a tert-butyl group was used instead of the benzyl ester of serine having the hydroxyl group protected with a tert-butyl group. The mass (m/z, MH$^+$) of this pentapeptide was m/z 444.3.

EXAMPLE 7

The epithelial cell growth promoters of Examples 1 to 4 were subjected to a cell growth test for murine HBKs, respectively. The following culture medium and test medium were used.

| (a) Culture medium | |
|---|---|
| DMEM (product code "D-5523", a product by Sigma) | |
| FBS (product code "10100756", a product by Cansera International Inc.) | 10% |
| Penicillin/streptomycin (product code "15140-122", a product by GIBCO) | 1% |
| (b) Test medium | |
| MCDB153 (product code "M7403", a product by Sigma) | |
| Insulin (product code "16634", bovine, a product by Sigma) | 5 µg/ml |
| Apo-transferrin (product code "T1147", human, a product by Sigma) | 10 µg/ml |
| EGF (product code "01-101", murine, a product by Upstate Biotechnology Inc.) | 5 ng/ml |
| BPE (product code "13028-014", bovine pituitary extract, a product by GIBCO) | 35 µg/ml |
| Water-soluble hydrocortisone (product code "174-00", a product by NACALAI TESQUE INC.) | 0.5 µg/ml |
| Ethanolamine (product code "012-12455", a product of Wako Pure Chemical Industries Ltd.) | 100 µM |
| o-phosphorylethanolamine (product code "P0503", a product by Sigma) | 100 µM |

(1) Isolation and Culture of HBKs

The skin of a 5 day-old mouse was cut with a scalpel into strips of approximately 2-mm-wide skin slices, which were in turn immersed in a solution prepared by dissolving dispase (lot No. 0101, a product by GODO SHUSEI CO.) at a proportion of 500 U/ml in DMEM (product code "D-5523", a product by Sigma) containing FBS (product code "10100756", a product by Cansera International Inc.) in a concentration of 5%, and then kept standing at 4° C. for 16 hours. Subsequently, the epidermis was ablated and removed with tweezers from the skin slices to collect only dermis tissues. The thus obtained dermis tissues were immersed in PBS (−) (product code "P-4417", a product by Sigma) and cut into strips with ophthalmological scissors. The thus obtained strips were immersed in a solution prepared by dissolving collagenase (lot No. 001014W, a product by Nitta Gelatin Inc.) in a concentration of 0.2% in DMEM containing FBS in a concentration of 5%, and then digested at 37° C. for 1 hour.

After centrifugation at 1000 rpm for 5 minutes, the supernatant was removed, and the residue was supplemented with PBS (−) and gently pipetted to prepare a dermis suspension.

For separating dermal fibroblasts and hair bulbs, the dermis suspension was kept standing for 15 minutes to precipitate only the hair bulbs. The hair bulbs obtained by repeating the "standing to precipitation" procedure three times were immersed in a solution prepared by dissolving, in 2.65 mM EDTA aqueous solution, trypsin in a concentration of 0.25%, and then treated at 37° C. for 5 minutes to prepare a dispersion solution of HBKs.

Next, this dispersion solution was centrifuged at 1000 rpm for 5 minutes. After this centrifugation, the supernatant was removed. The thus obtained HBKs were dispersed in a culture medium, then inoculated into a collagen-coated 96-well microplate, and cultured at 37° C. in an atmosphere containing 5% $CO_2$.

(iii) Results

Figure 7:
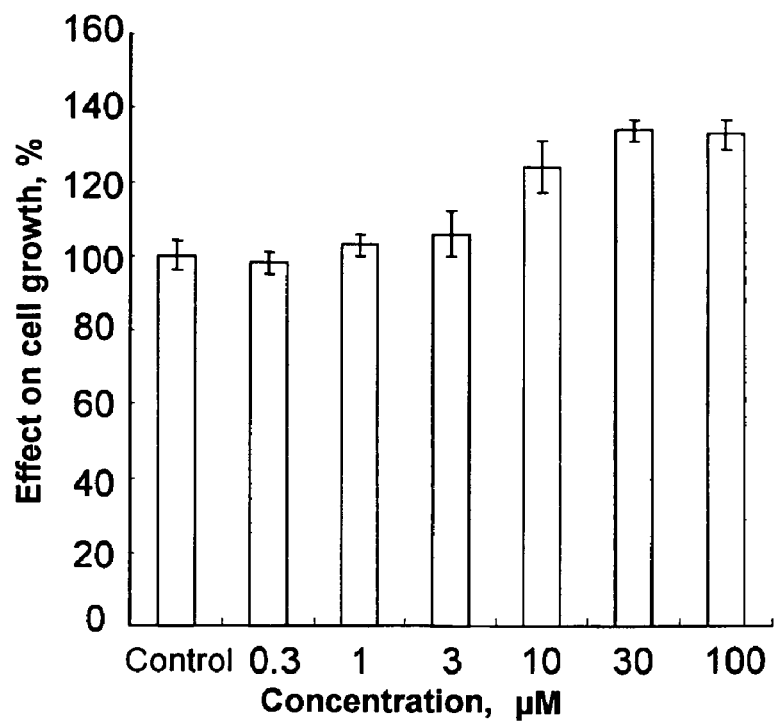
FIG. 7 is a bar graph showing the effect of the IGS obtained in Example 7 on HBKs growth.

As seen in FIG. 7, the cell growth effects on IGS in concentrations of 0.3, 1, 3, 10, 30, and 100 μM were 98, 103, 106, 124, 134, and 133%, respectively, as compared with that on the control. Significant difference ($p<0.01$ in all the cases) could be noted when the concentration was 10 μM or higher.

Figure 8:
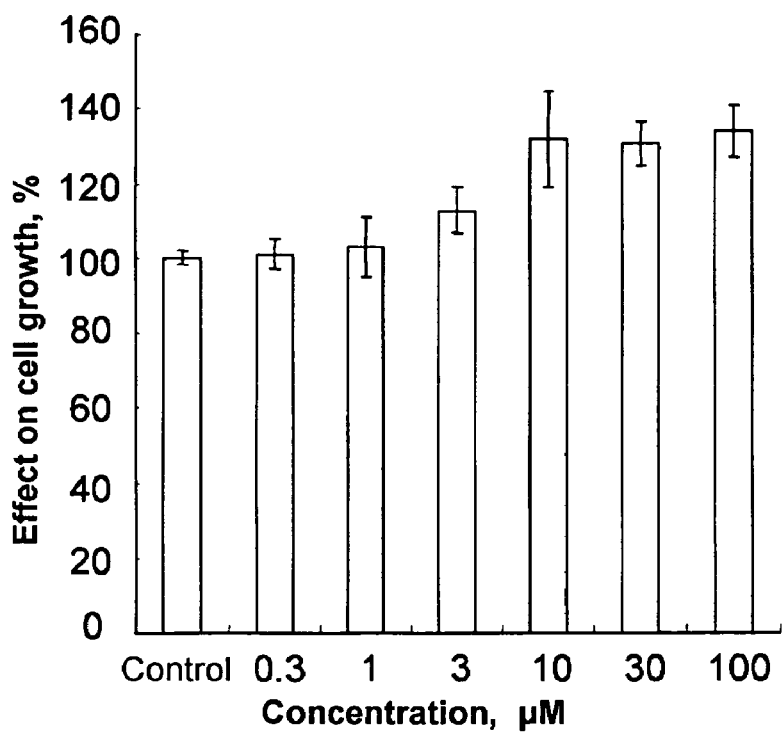
FIG. 8 is a bar graph showing the effect of the PIG obtained in Example 7 on HBKs growth.

As seen in FIG. 8, the cell growth effects on PIG in concentrations of 0.3, 1, 3, 10, 30, and 100 μM were 101, 103, 113, 132, 131, and 134%, respectively, as compared with that on the control. Significant difference (3 μM: $p<0.05$; 10, 30, and 100 μM: $p<0.01$) could be noted when the concentration was 1 μM or higher.

Figure 9:
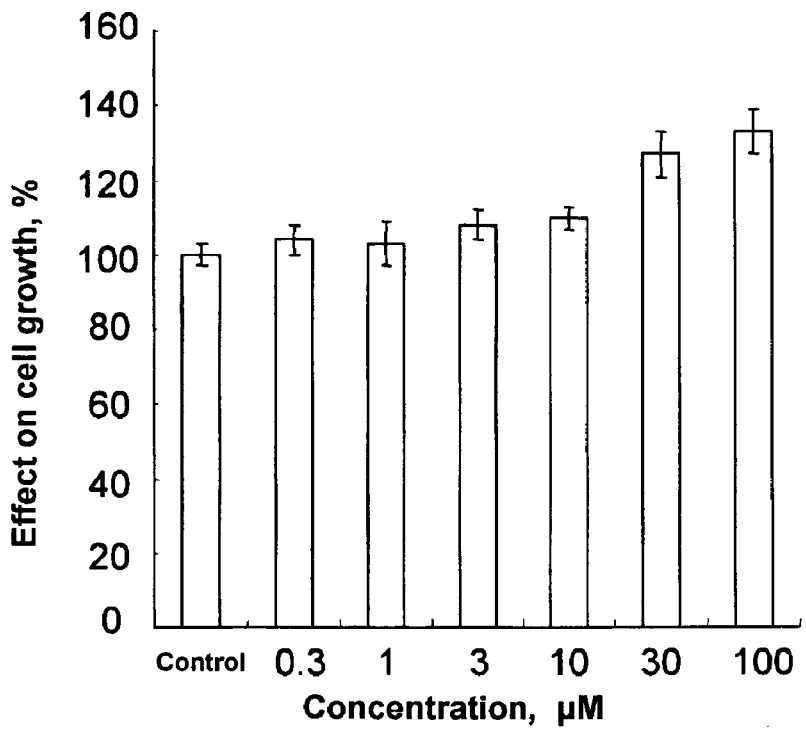
FIG. 9 is a bar graph showing the effect of the PIGS obtained in Example 7 on HBKs growth.

As seen in FIG. 9, the cell growth effects on PIGS in concentrations of 0.3, 1, 3, 10, 30, and 100 μM were 104, 103, 108, 110, 127, and 133%, respectively, as compared with that on the control. Significant difference (3 and 10 μM: $p<0.05$; 30 and 100 μM: $p<0.01$) could be noted when the concentration was 3 μM or higher.

Figure 10:
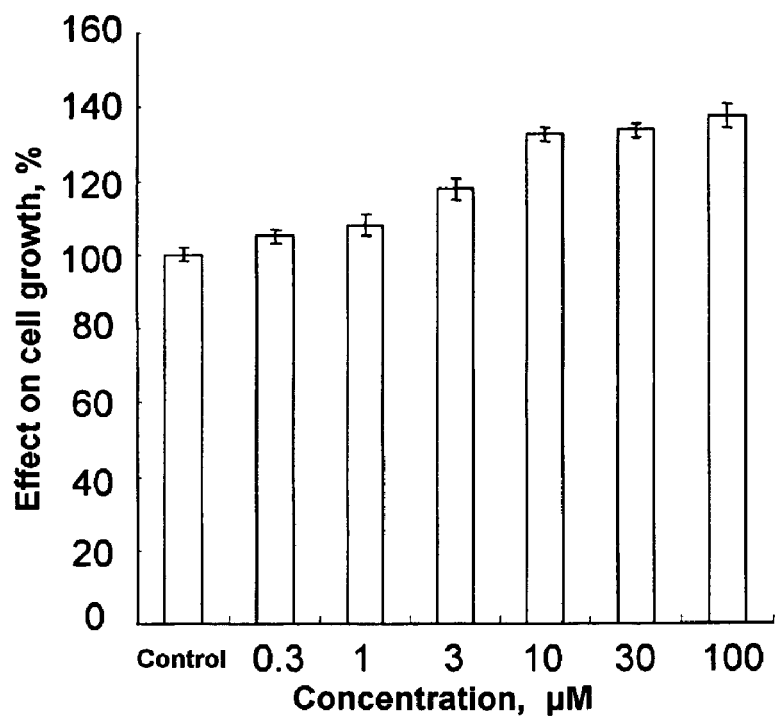
FIG. 10 is a bar graph showing the effect of the GPIG obtained in Example 7 on HBKs growth.

As seen in FIG. 10, the cell growth effects on GPIG in concentrations of 0.3, 1, 3, 10, 30, and 100 μM were 105, 108, 118, 133, 134, and 138%, respectively, as compared with that on the control. Significant difference (0.3 μM: $p<0.05$; 1, 3, 10, 30, and 100 μM: $p<0.01$) could be noted when the concentration was 0.3 μM or higher.

The test was further conducted on epidermal cells, dermal fibroblasts and hair papilla cells to find that the epithelial cell growth promoter of the present invention exhibited the same cell growth-promoting effect on the epidermal cells as that on the HBKs along with no influence on the dermal fibroblasts and the hair papilla cells.

EXAMPLE 8

A 1 mg portion of the pentapeptide obtained in Example 5 was dissolved in 300 μl of water for injection (product code "057-00456", a product by Otsuka Pharmaceutical Co.), to which 200 μl of propylene glycol (product code "161-05006", a product by Wako Pure Chemical Industries) and 500 μl of ethyl alcohol (product code "057-00456", a product by Wako Pure Chemical Industries) were then added and they were mixed together to prepare an epithelial cell growth promoter in a concentration of 1 mg/ml.

(2) Cell Growth Test (i) Sample Preparation

The isoleucyl-glycyl-serine (hereinafter, abbreviated to IGS), prolyl-isoleucyl-glycine (hereinafter, abbreviated to PIG), prolyl-isoleucyl-glycyl-serine (SEQ ID NO: 2) (hereinafter, abbreviated to PIGS), and glycyl-prolyl-isoleucyl-glycine (SEQ ID NO: 1) (hereinafter, abbreviated to GPIG) obtained in Examples 1 to 4 were separately dissolved in a test media to prepare 6 types of sample solutions each in a concentration of 0.3 μM, 1 μM, 3 μM, 10 μM, 30 μM, and 100 μM. Only a test medium was used as a control.

(ii) HBK Growth Test

After 24 hours from the inoculation of the cells, the culture solutions were removed, and the cultured cells were washed with an MCDB153 solution. Each of the above-mentioned sample solutions was added to the cultured cell at 100 μl/well and cultured at 37° C. in an atmosphere containing 5% $CO_2$.

After 4 days, AlamarBlue reagent (registered trademark, cat. No. DAL1100, lot No. AB083002, a product by Biosource International Inc.) was added at 10 μl/well, and the culture was continued at 37° C. in a 5% $CO_2$ atmosphere. After culturing for 2 hours, fluorescence intensity (excitation wavelength: 544 nm, measurement wavelength: 590 nm) was measured with a microplate reader (Model "Fluoroskan Ascent FL", manufactured by Labsystems) to evaluate the number of cells.

Incidentally, the evaluation was performed by calculating the ratios (percentage) of the degrees of cell growth for the peptides obtained in Examples 1 to 4 relative to the degree of cell growth for the control and indicating the cell growth ratios by mean value±standard deviation (n=5). A significant difference test was performed by Dunnett's multiple comparison test (software "SuperANOVA V. 1.11", a product by Abacus Concepts). When a significance level was less than 5% ($p<0.05$), it was concluded that there was significant difference. The results with the IGS, the results with the PIG, the results with the PIGS and the results with the GPIG obtained in this way are shown as bar graphs in FIG. 7, FIG. 8, FIG. 9, and FIG. 10, respectively.

Ten 7-week-old C3H/He female mice were raised for acclimatization for 1 week, and the hair on the dorsal of each mouse in the telogen phase of a hair cycle was shaved with an electric clipper and an electric shaver to prepare experimental animals.

Next, these experimental animals were divided into two groups each containing five mice. The epithelial cell growth promoter was applied at 100 μl/mouse once a day to the shaved area of the first group from the 3rd day after shaving on, while only a mixture of water for injection, propylene glycol, and ethyl alcohol (3:2:5 by volume) was applied as a control to the second group. When pictures of the shaved areas were taken with a digital camera on the 14th day after application, evident hair growth promotion was observed in the group (B) with application of the epithelial cell growth promoter of the present invention, as compared with that observed in the control group (A).

Next, these images were computer-processed to calculate with image analysis software the ratio of the hair-regrowth area (the number of pixels of hair-regrowth area/the number of pixels of shaved area) as percentages. A significant difference test was performed by Student's t test (software "StatVIEW J-4.02", a product by Abacus Concepts). When a significance level was less than 5% ($p<0.05$), it was concluded that there was significant difference.

Figure 11:
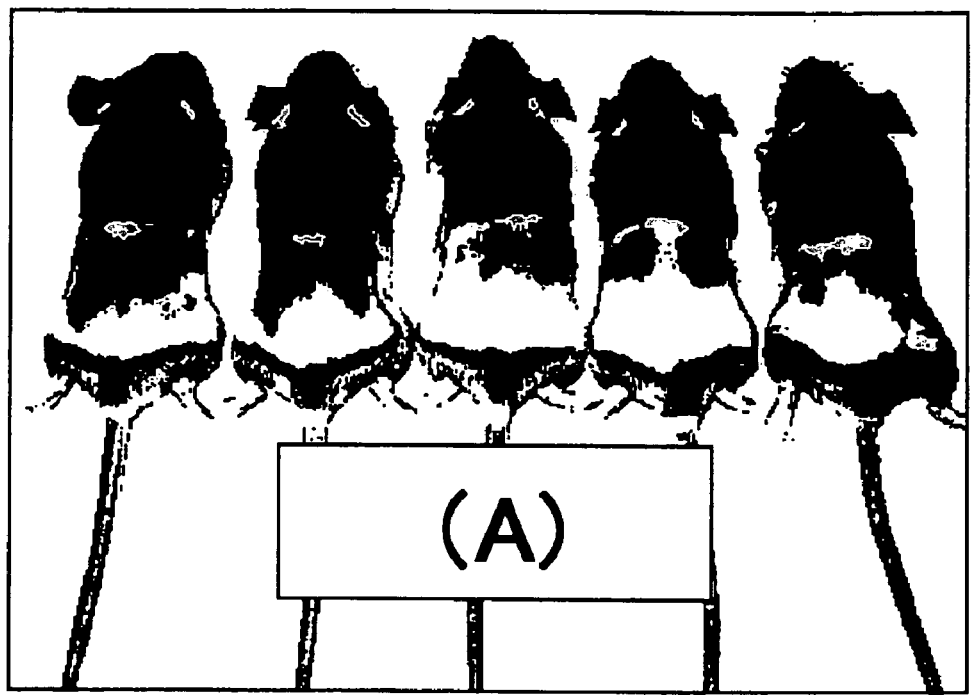
FIG. 11 includes computer-processed diagrams of photographs taken with a digital camera and showing the shaved areas with the group (B) coated with application of the epithelial cell growth promoter obtained in Example 8 and the control group (A) on the 14th day from which the ratio of the hair-regrowth area was calculated as percentages using an image analysis software.
Figure 11:
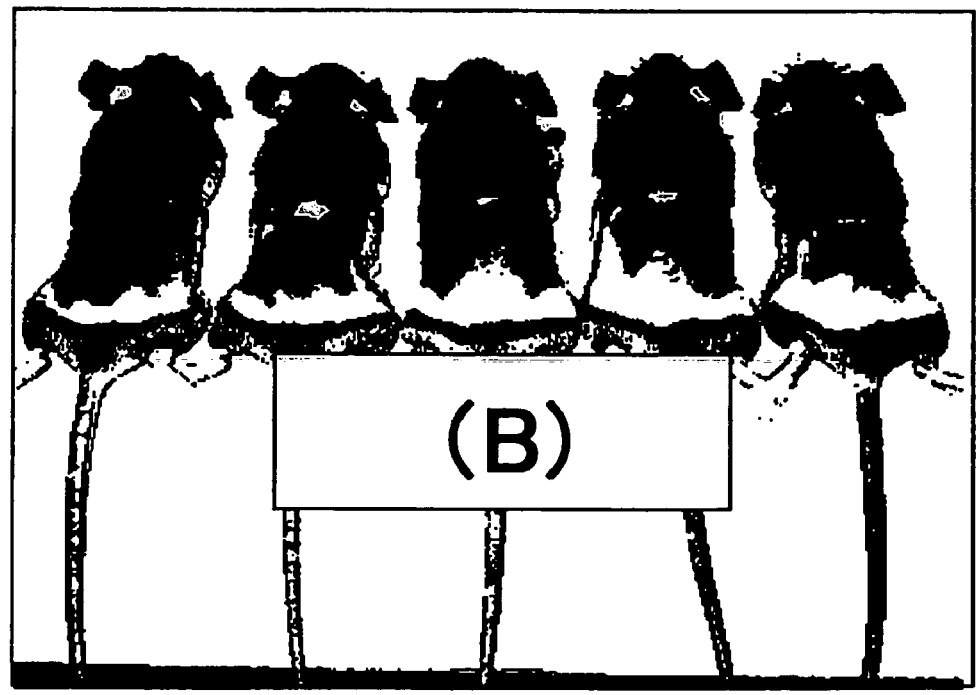

The results are shown in FIG. 11. In this figure, white portions represent unhaired portions, and black portions represent haired portions. As seen from the results, the ratio of the hair-regrowth area of the control group (A) was 36.9±5.7%, whereas the ratio of the hair-regrowth area of the group (B) with application of the epithelial cell growth promoter of the present invention was 66.6±3.5%, to show that the epithelial cell growth promoter of the present invention promoted hair regeneration significantly ($p<0.01$).

EXAMPLE 9

To confirm the cell selectivity of the oligopeptide obtained in Example 5 as an epithelial cell growth promoter, the presence or absence of the cell growth-promoting effect on cells existing in skin tissues, that is, HBKs, epidermal cells, dermal fibroblasts, and hair papilla cells, was examined in the following manner. Incidentally, the same culture medium and test medium as in Example 7 were used.

(1) Preparation of HBKs, Epidermal Cells, Dermal Fibroblasts, and Hair Papilla Cells The skin of a 5 day-old C3H/HeN mouse was aseptically collected and cut with a surgical knife into samples of strips of approximately 2-mm-wide skin slices. The above-mentioned samples were immersed in a solution prepared by dissolving 500 U/ml of dispase (lot No. 0101, a product by GODO SHUSEI CO.) in DMEM (product code "D-5523", a product by Sigma) containing 5% by mass of FBS (lot No. 0101, a product by Cansera International Inc.), and then kept standing at 4° C. for 16 hours. Subsequently, epidermis tissues were ablated with tweezers from the skin slices and separated from dermis tissues. The thus obtained epidermis tissues were subjected to the separation of epidermal cells, and the dermis tissues were subjected to the separation of HBKs and dermal fibroblasts.

The thus obtained dermis tissues were immersed in PBS (−) (product code "P-4417", a product by Sigma) and cut into strips with ophthalmological scissors. The strips were immersed into a solution prepared by dissolving 0.2% by mass of collagenase (lot No. 001014W, a product by Nitta Gelatin Inc.) in DMEM containing 5% by mass of FBS, and then digested at 37° C. for 1 hour. The thus obtained dermis digestion solution was centrifuged at 1000 rpm for 5 minutes. The supernatant was removed, and the residue was supplemented with PBS (−) and gently pipetted to prepare a dermis suspension.

For separating dermal fibroblasts and hair bulbs, this dermis suspension was kept standing for 15 minutes to precipitate only the hair bulbs. The "standing to precipitation" procedure was repeated three times. The thus obtained hair bulbs were immersed in a solution preparing by dissolving 0.25% by mass of trypsin in 2.65 mM aqueous EDTA solution, and then treated at 37° C. for 5 minutes to prepare a dispersion solution of HBKs.

Next, this dispersion solution was centrifuged at 1000 rpm for 5 minutes. After this centrifugation, the supernatant was removed. The thus obtained HBKs were dispersed in a culture medium, then inoculated into a collagen-coated 96-well microplate, and cultured at 37° C. in an atmosphere containing 5% $CO_2$.

On the other hand, dermal fibroblasts floating in the supernatant by the first "standing to precipitation" procedure were collected and centrifuged at 1000 rpm for 5 minutes. After this centrifugation, the supernatant was removed. The thus obtained dermal fibroblasts were dispersed in a culture medium, then inoculated into a 96-well microplate, and cultured at 37° C. in an atmosphere containing 5% $CO_2$.

The above-mentioned epidermis tissues were immersed in a solution prepared by dissolving 0.25% by mass of trypsin in 2.65 mM aqueous EDTA solution, and then treated at 37° C. for 5 minutes to prepare a dispersion solution of epidermal cells.

Subsequently, this dispersion solution was centrifuged at 1000 rpm for 5 minutes, and the supernatant was removed. The thus obtained epidermal cells were dispersed in a culture medium, then inoculated into a collagen-coated 96-well microplate, and cultured at 37° C. in an atmosphere containing 5% $CO_2$.

Moreover, human hair papilla cells (product code "602-05", a product by TOYOBO CO.) were dispersed in a culture medium, then inoculated into a collagen-coated 96-well microplate, and cultured at 37° C. in an atmosphere containing 5% $CO_2$.

(2) Cell Growth Test (i) Sample Preparation

A 1 mg portion of the pentapeptide obtained in Example 5 was added to 232.8 µl of a test medium and dissolved by stirring to prepare a 10 mM solution. Subsequently, this 10 mM solution was stepwise diluted to prepare 6 types of sample solutions each in a concentration of 100 µM (No. 1), 30 µM (No. 2), 10 µM (No. 3), 3 µM (No. 4), 1 µM (No. 5), and 0.3 µM (No. 6). Only a test medium was used as a control.

(ii) HBK and Epidermal Cell Growth Tests

After 24 hours from the inoculation of the cells, the culture solutions were removed, and the cultured cells were washed with an MCDB153 solution. Each of the above-mentioned sample solutions was added to the cultured cell at 100 µl/well and cultured at 37° C. in an atmosphere containing 5% $CO_2$. After 4 days, AlamarBlue reagent (registered trademark, cat. No. DAL1100, lot No. AB083002, a product by Biosource International Inc.) was added at 10 µl/well, and the culture was continued at 37° C. in an atmosphere containing 5% $CO_2$. After 2 hours, fluorescence intensity (excitation wavelength: 544 nm, measurement wavelength: 590 nm) was measured with a microplate reader (Model "Fluoroskan Ascent FL", manufactured by Labsystems) to evaluate the number of cells. A significant difference test was performed by Dunnett's multiple comparison test (software "Super ANOVA V. 1.11", a product by Abacus Concepts). When a significance level did not exceed 5% ($p<0.05$), it was concluded that there was significant difference.

Figure 12:
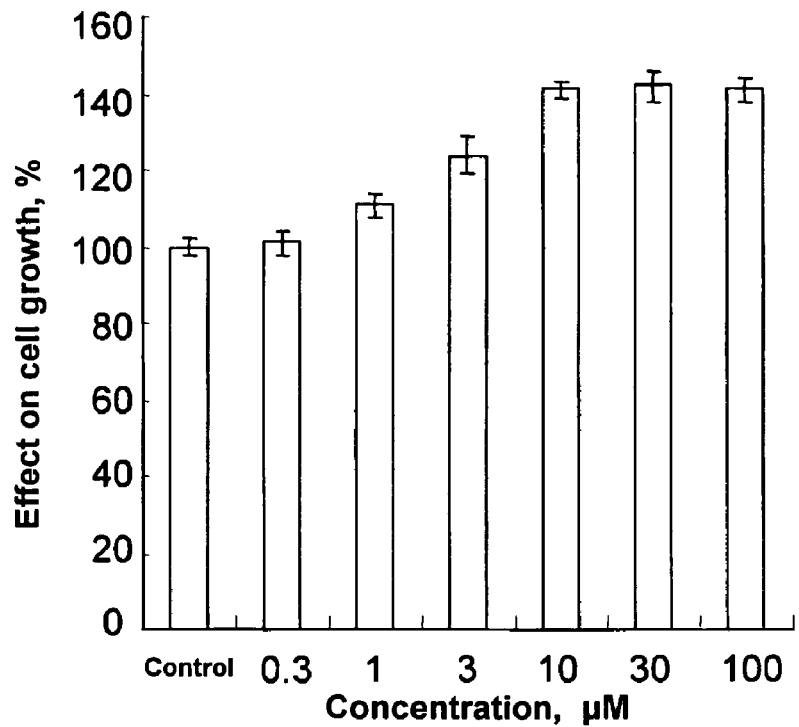
FIG. 12 is a bar graph showing the effect of cell growth on the HBKs obtained in Example 9.
Figure 13:
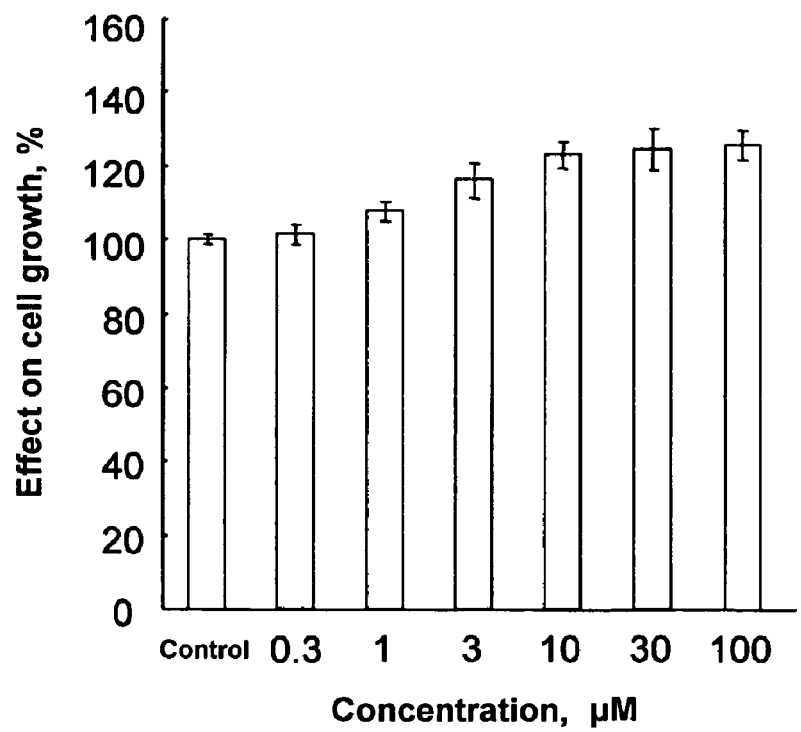
FIG. 13 is a bar graph showing the effect of cell growth on the epidermal cells obtained in Example 9.

The results of the HBK growth tests and the results of the epidermal cell growth tests obtained in this way are each shown as bar graphs in FIG. 12 and FIG. 13.

(iii) Dermal Fibroblast and Hair Papilla Cell Growth Tests

After 24 hours from the inoculation of the cells, the culture solutions were removed, and the cultured cells were washed with a DMEM solution. Each of the above-mentioned sample solutions was added to the cultured cell at 100 µl/well and cultured at 37° C. in an atmosphere containing 5% $CO_2$. Moreover, culturing was performed in the same manner with a culture medium as a positive control. After 3 days, AlamarBlue reagent (product code "341-077612", a product by Biosource International Inc.) was added at 10 µl/well, and the culture was further continued at 37° C. in an atmosphere containing 5% $CO_2$. After 2 hours, fluorescence intensity (excitation wavelength: 544 nm, measurement wavelength: 590 nm) was measured with a microplate reader (Model "Fluoroskan Ascent FL", manufactured by Labsystems) to evaluate the number of cells.

Figure 14:
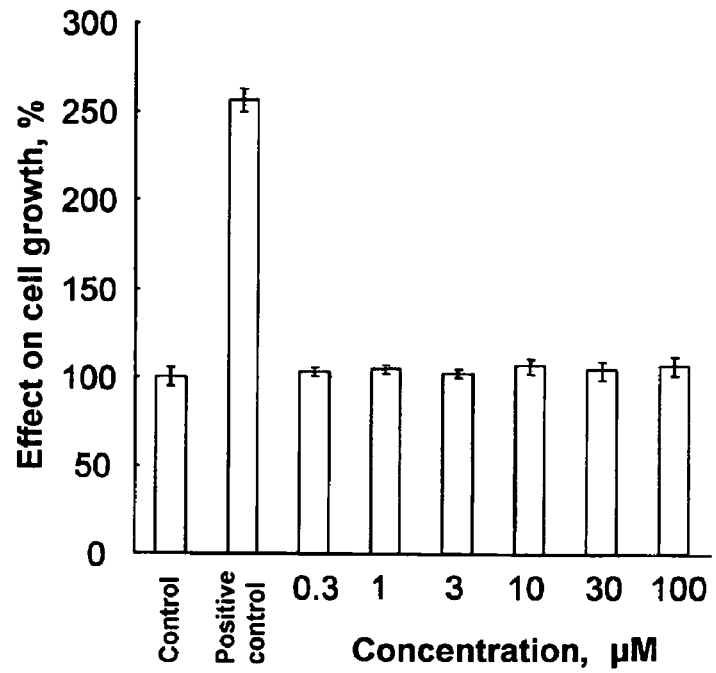
FIG. 14 is a bar graph showing the effect of cell growth on the dermal fibroblasts obtained in Example 9.
Figure 15:
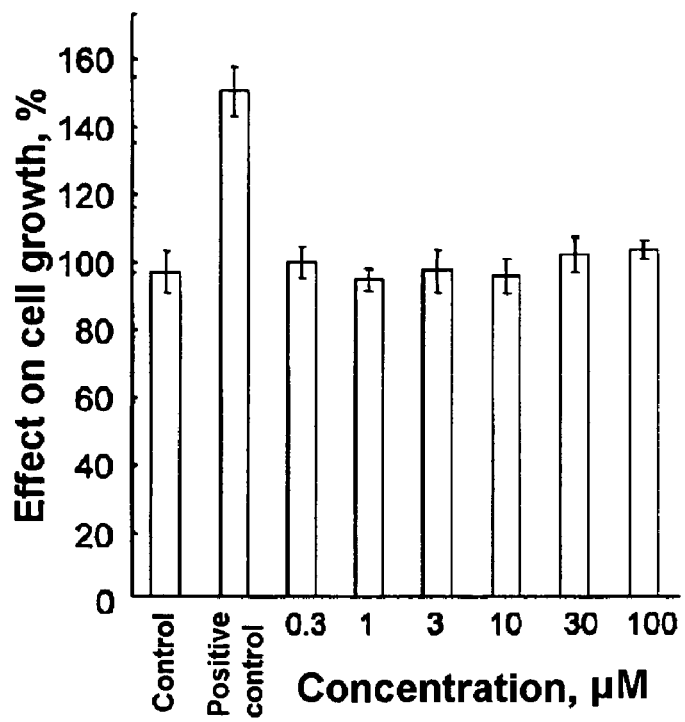
FIG. 15 is a bar graph showing the effect of cell growth on the hair papilla cells obtained in Example 9.

The results of the dermal fibroblast growth tests and the results of the hair papilla cell growth tests obtained in this way are each shown as bar graphs in FIG. 14 and FIG. 15.

(iv) Results

As seen in FIG. 12, the effects of the sample solutions on the HBK growth were 101% (No. 6), 111% (No. 5), 124%

(No. 4), 141% (No. 3), 142% (No. 2), and 141% (No. 1), respectively, as compared with that of the control. Significant difference (p<0.01) could be noted when the concentration was 1 µM or higher.

This demonstrated that the epithelial cell growth promoter of Example 5 dose-dependently exhibited the HBK growth-promoting effect in a concentration of 1 µM or higher.

As seen in FIG. 13, the effects of the sample solutions on the epidermal cells were 102% (No. 6), 110% (No. 5), 118% (No. 4), 124% (No. 3), 127% (No. 2), and 127% (No. 1), respectively, as compared with that of the control. Significant difference (1 µM: p<0.05, 3 µM or higher: p<0.01) could be noted when the concentration was 1 µM or higher.

This demonstrated that the epithelial cell growth promoter of Example 5 dose-dependently exhibited the growth-promoting effect on epidermal cells as well as HBKs in a concentration of 1 µM or higher.

On the other hand, as seen in FIGS. 14 and 15, the epithelial cell growth promoter of Example 5 was shown to have no influence on dermal fibroblasts and hair papilla cells.

These facts demonstrated that the epithelial cell growth promoter of Example 5 exhibited selective cell growth-promoting effect on HBKs and epidermal cells classified into epithelial cells.

In this way, the epithelial cell growth promoter of the present invention exhibits selective cell growth-promoting effect on HBKs and epidermal cells classified into epithelial cells so as not adversely to affect cells other than epithelial cells constituting skin tissues, when used as a liniment such as, for example a lotion.

INDUSTRIAL APPLICABILITY

The compound of the present invention can be employed as an epithelial cell growth promoter for hair growth and skin regeneration. According to the present invention, a novel excellent epithelial cell growth promoter having not only hair growth effect but also skin regeneration effect and therapeutic effect on atopic dermatitis is provided.

The invention claimed is:

1. A water-soluble peptide consisting of glycyl-prolyl-isoleucyl-glycyl-serine [SEQ ID NO: 3] or glycyl-prolyl-isoleucyl-glycyl-threonine [SEQ ID NO: 4], or a water-soluble salt thereof.

2. The water-soluble peptide according to claim 1, wherein the peptide is glycyl-prolyl-isoleucyl-glycyl-serine [SEQ ID NO: 3], or a water-soluble salt thereof.

3. The water-soluble peptide according to claim 1, wherein the peptide is glycyl-prolyl-isoleucyl-glycyl-threonine [SEQ ID NO: 4], or a water-soluble salt thereof.

4. A composition comprising the water-soluble peptide according to claim 1, or a water-soluble salt thereof, in combination with a carrier.

* * * * *